United States Patent
Ouyang et al.

(10) Patent No.: US 7,144,709 B2
(45) Date of Patent: *Dec. 5, 2006

(54) DIAGNOSTICS BASED ON TETRAZOLIUM COMPOUNDS

(75) Inventors: Tianmei Ouyang, Fremont, CA (US); Yeung Siu Yu, Pleasanton, CA (US)

(73) Assignee: LifeScan, Inc., Milpitas, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/990,684

(22) Filed: Nov. 16, 2004

(65) Prior Publication Data

US 2005/0112712 A1    May 26, 2005

Related U.S. Application Data

(60) Division of application No. 10/663,217, filed on Sep. 15, 2003, now Pat. No. 7,011,954, which is a division of application No. 09/513,071, filed on Feb. 25, 2000, now Pat. No. 6,656,697, which is a continuation-in-part of application No. 09/282,083, filed on Mar. 30, 1999, now Pat. No. 6,200,773, which is a continuation-in-part of application No. 09/161,876, filed on Sep. 28, 1998, now Pat. No. 5,902,731.

(51) Int. Cl.
  *G01N 33/53* (2006.01)

(52) U.S. Cl. .................. 435/7.9; 435/14; 435/25; 435/287.7; 435/287.8; 435/96.2; 435/970; 436/110; 436/537; 422/56; 422/57

(58) Field of Classification Search ............... 435/7.9, 435/14, 26, 287.7, 287.8, 96.2, 970; 436/110, 436/537; 422/56, 57
See application file for complete search history.

(56) References Cited

U.S. PATENT DOCUMENTS

| | | | |
|---|---|---|---|
| 3,791,988 | A | 2/1974 | Josef et al. |
| 3,964,974 | A | 6/1976 | Banauch et al. |
| 3,965,974 | A | 6/1976 | Sernetz et al. |
| 4,254,222 | A | 3/1981 | Owen |
| 4,366,243 | A | 12/1982 | Rupchock et al. |
| 4,461,829 | A | 7/1984 | Greenquist |
| 4,472,498 | A | 9/1984 | Masuda et al. |
| 4,613,569 | A | 9/1986 | Geisler et al. |
| 4,629,697 | A | 12/1986 | Limbach et al. |
| 4,803,158 | A | 2/1989 | Shigeta et al. |

(Continued)

FOREIGN PATENT DOCUMENTS

DE    4 11 464    10/1994

(Continued)

OTHER PUBLICATIONS

Al-Bekairi et al., (1994), *Biochemistry and Molecular Biology International*, 34:(2)233-238.

(Continued)

*Primary Examiner*—Long V. Le
*Assistant Examiner*—Pensee T. Do
(74) *Attorney, Agent, or Firm*—Kagan Binder PLLC

(57) ABSTRACT

A reagent is suitable for measuring the concentration of an analyte in a hemoglobin-containing biological fluid, such as whole blood. The reagent comprises a flavin-dependent enzyme that has specificity for the analyte, a flavin cofactor if, and only if, a flavin is not bound to the enzyme, a tetrazolium dye precursor, an electron transfer agent, and a nitrite salt. The reagent causes dye formation that is a measure of the analyte concentration. The nitrite salt suppresses interfering dye formation caused non-enzymatically by the hemoglobin. Preferably, the reagent is used in a dry strip for measuring glucose in whole blood.

4 Claims, 4 Drawing Sheets

U.S. PATENT DOCUMENTS

| | | | |
|---|---|---|---|
| 4,824,779 | A | 4/1989 | Aoyama et al. |
| 4,966,856 | A | 10/1990 | Ito et al. |
| 4,994,382 | A | 2/1991 | Ameyama et al. |
| 5,126,247 | A | 6/1992 | Palmer et al. |
| 5,166,051 | A | 11/1992 | Killeen et al. |
| 5,178,831 | A | 1/1993 | Sakota et al. |
| 5,196,519 | A | 3/1993 | Mooberry |
| 5,206,147 | A | 4/1993 | Hoenes |
| 5,236,567 | A | 8/1993 | Nanba et al. |
| 5,278,047 | A | 1/1994 | Lilia et al. |
| 5,298,144 | A | 3/1994 | Spokane |
| 5,304,468 | A | 4/1994 | Phillips et al. |
| 5,340,722 | A | 8/1994 | Wolfbeis et al. |
| 5,360,595 | A | 11/1994 | Bell et al. |
| 5,484,708 | A | 1/1996 | Hoenes et al. |
| 5,510,245 | A | 4/1996 | Magers |
| 5,563,031 | A | 10/1996 | Yu |
| 5,902,731 | A | 5/1999 | Ouyang et al. |
| 5,948,695 | A | 9/1999 | Douglas et al. |
| 6,040,195 | A | 3/2000 | Carroll et al. |
| 6,162,639 | A | 12/2000 | Douglas |
| 6,200,773 | B1 | 3/2001 | Ouyang et al. |
| 6,420,128 | B1 | 7/2002 | Ouyang et al. |
| 6,656,697 | B1 | 12/2003 | Ouyang et al. |

FOREIGN PATENT DOCUMENTS

| | | |
|---|---|---|
| EP | 0239990 A2 | 3/1987 |
| EP | 0 279 988 | 9/1987 |
| EP | 0330517 B2 | 8/1989 |
| EP | 0654079 B1 | 5/1995 |
| EP | 0 476 454 | 10/1996 |
| EP | 0638805 A2 | 10/2001 |
| EP | 0908453 B1 | 6/2002 |
| FR | 2520380 | 7/1983 |
| JP | 60/24199 | 2/1985 |
| SG | 9901673-5 | 3/1999 |
| SG | 9902107-3 | 11/2003 |
| SU | 2 050 546 | 4/1990 |
| WO | WO 94/01544 | 1/1994 |
| WO | WO 94/01578 | 1/1994 |

OTHER PUBLICATIONS

Bruchhaus et al., "Recombinant expression and biochemical characterization of an NADPH: flavin oxidoreductase from *Entamoeba histolytica*," Biochem. J. 330: 1217-1221, 1998.

Lindquist et al. (1989), *Clinical Chem.*, 35(4):617-619.

Gunn and Forget, (1968), *Haemoglobin: Molecular, Genetic and Clinical Aspects*, W.B. Saunders Co., Philadelphia, PA, 638-644.

Ketosite Test (1993) from GDS Diagnostics, Elkhart, IN, Dec. 29 (8 pages).

Glucometer Encore Blood Glucose Test Strips, Distributed by Miles Canada, Inc., Diagnostics Division, Etobiocoke, Ontario M9W 1G6, 1992 (2 pages).

Tietz Textbook of Clinical Chemistry, $2^{nd}$ Ed. ed. C. Curtis et al., W.B. Saunders Co. Philadelphia, PA, 1994, pp. 974-978 and 1174-1175.

Sock J et al., "Analytical Biochemistry", vol. 171, No. 2, 1988, pp. 310-319.

Letter dated Jun. 2, 2004 from Tsar & Tsai Law Firm in Taiwan to Johnson & Johnson re ROC Application No. 90122526.

Letter dated Jun. 2, 2004 from Tsar & Tsai Law Firm in Taiwan to Johnson & Johnson re ROC Application No. 90104406.

Claus et al., "Atypical (Mild) forms of dihydropteridine reductase deficiency: neurochemical evaluation and mutation detection," Pediatric Research, vol. 32, No. 6, 1992.

Hartmann et al., "Spectroscopic detection of chemical intermediates in the reaction of para-substituted benzlamines with bovine serum amine oxidase," Biochemistry 32, 2234-2241, 1993.

Blau et al."Atypical (Mild) Forms of Dihydropterdine Reductase Deeficiency: Neurochemical Evaluation and Mutation Detection" Pediactric Research vol. 32, No. 6, 1992.

English Abstract of Japanese Patent Application 60024199, Published Feb. 6, 1985, Nippon Chemipher KK.

English Abstract of French Patent Application 2520380, Published Jul. 29, 1983, Tokyo Jozo KK.

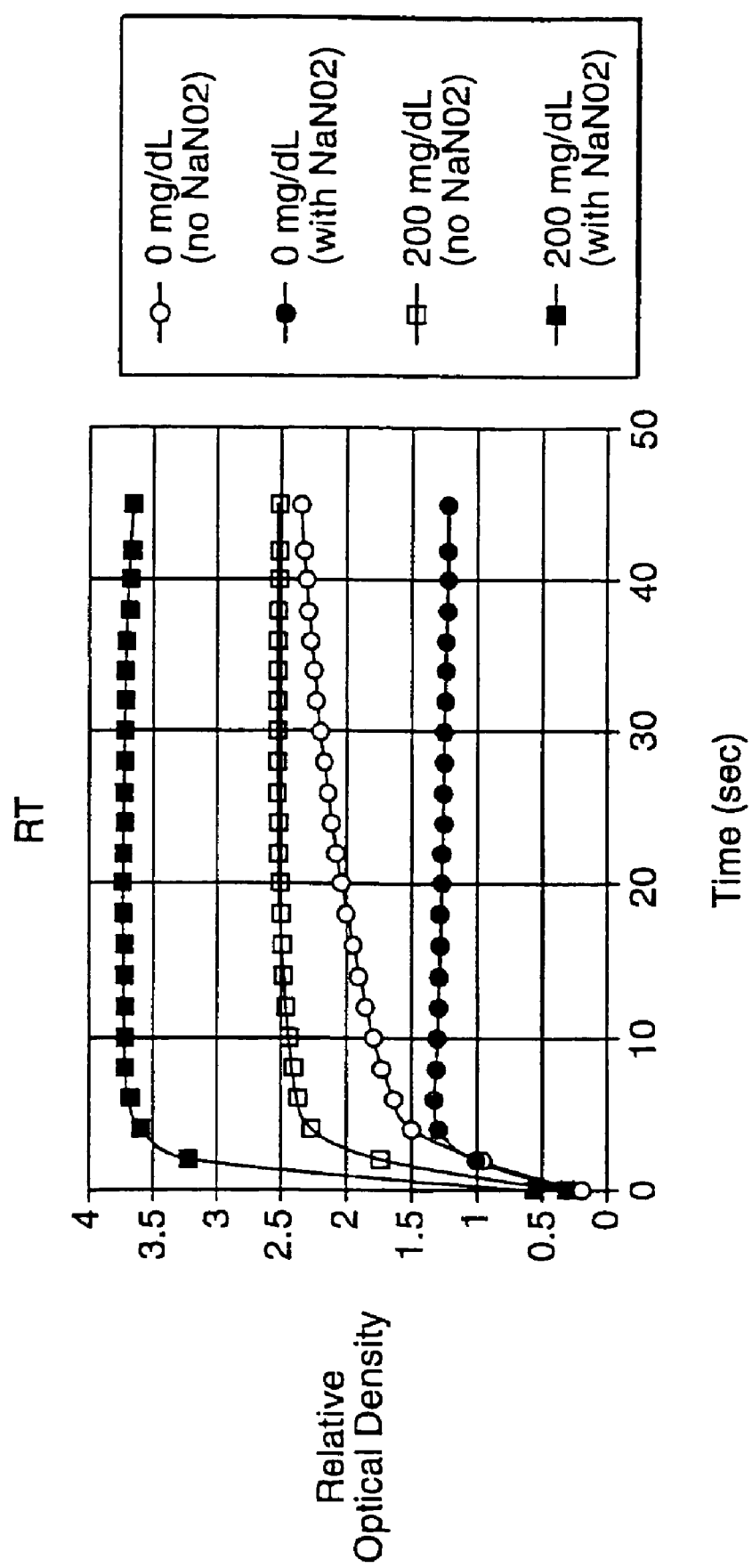

DIAGNOSTICS BASED ON TETRAZOLIUM COMPOUNDS

CROSS-REFERENCE TO PRIOR APPLICATION

This application is a divisional of U.S. patent application Ser. No. 10/663,217, filed Sep. 15, 2003, now U.S. Pat. No. 7,011,954, which is a divisional of U.S. patent application Ser. No. 09/513,071, filed Feb. 25, 2000, now U.S. Pat. No. 6,656,697, which is a continuation-in-part of U.S. application Ser. No. 09/282,083, filed Mar. 30, 1999, now U.S. Pat. No. 6,200,773, which is a continuation-in-part of U.S. Ser. No. 09/161,876, filed on Sep. 28, 1998, now U.S. Pat. No. 5,902,731, the disclosures of which are herein incorporatea by reference.

BACKGROUND OF INVENTION

1. Field of the Invention

This invention relates to diagnostic compositions that permit the measurement of analyte concentrations in hemoglobin-containing biological fluids. The compositions are based on tetrazolium dye precursors and involve suppressing the hemoglobin-induced reduction of them.

2. Description of the Related Art

Adipose tissue is one of the most abundant forms of energy storage in the body. It releases stored fatty acids into the circulatory system to be metabolized primarily by the liver. In the process, fat is consumed and energy is released and made available to the body. Normally, little fat is consumed, the fatty acids are completely metabolized to carbon dioxide and water, and the conversion does not upset the delicate pH balance of the body. However, if insufficient amounts of carbohydrates are present in the body, due, for example, to dieting, then fat consumption and fatty acid production can increase to potentially harmful levels. In addition to dieters, insulin-dependent patients are vulnerable, because of their impaired carbohydrate metabolism. When excessive fatty acid is used to supply a body's energy demand, then large quantities of acetoacetate, acetone, and beta-hydroxybutyrate are produced. These intermediates are referred to as ketone bodies, and the condition is known as ketoacidosis.

The ketone bodies can normally be recycled into other forms by the body, provided it is not overwhelmed. Therefore, a healthy individual accumulates a negligible amount of these analytes. When a large quantity of fats is being metabolized in a relatively short period or when most of the energy is derived from fats, massive amounts of ketone bodies are produced. Excessive production of these fat metabolites can cause certain neurologic disorders, if the problem is not corrected promptly.

Ketone bodies are present in blood and, if a threshold is exceeded, are excreted via the urine. They are easily detected by a modern clinical analyzer. On average, the percentages of beta-hydroxybutyrate, acetoacetate, and acetone are 78%, 20% and 2%, respectively. Because of its relatively low concentration and high volatility, acetone is seldom measured. Instead, acetoacetate is quantitatively determined by a nitroprusside reaction and the beta-hydroxybutyrate is quantified with an enzymatic method. Acetoacetate test strips have been available for decades. They are based on a nitroprusside ion coupling reaction with aldehydes and ketones. An alkaline urine sample or a serum specimen is allowed to react with the nitroprusside for some minutes; and a purple color is developed. The intensity of the color indicates the acetoacetate concentration. However, acetone interferes with the test, resulting in higher readings. Further, as the patient recovers from a ketoacidosis episode, the acetoacetate level in urine and in blood increases, thus making the diagnosis difficult.

The beta-hydroxybutyrate test is more useful for monitoring ketone body concentrations. It is based on the oxidation of beta-hydroxybutyrate with the corresponding dehydrogenase in the presence of nicotinamide adenine dinucleotide (NAD) cofactor. (Strictly speaking, only D-beta-hydroxybutyrate is naturally present and oxidized, but we omit the "D" for brevity throughout this specification and the appended claims.) Upon the oxidation, NADH is produced, and its concentration is measured directly with a UV spectrophotometer. Hence, the corresponding signal change in the spectrum is proportional to the analyte's concentration. Unfortunately, the excitation of NADH occurs in the UV region; thus, this mode of detection is suitable only for laboratory instruments. Another method for monitoring beta-hydroxybutyrate is by oxidizing the NADH with a tetrazolium compound.

Tetrazolium compounds are generally very sensitive to strong bases and to light. Thus, special care must be exercised to ensure the integrity of these compounds. Nevertheless, tetrazoliums have played an important role in studies of tissue metabolism. For example, this class of compounds has been used in probing anaerobic oxidation and reduction reactions in cells. Further, they are commonly used in clinical diagnostics. The compounds are typically light-colored or colorless compounds that undergo a reduction reaction, in the presence of a reducing agent, to yield a highly colored formazan. Reducing agents such as ascorbates, sulfhydryls, or variants of NADH, NADPH, PQQH$_2$ (reduced PQQ—pyrrolo-quinoline quinone), FMNH$_2$ (reduced FMN—flavin mononucleotide), and FADH$_2$ (reduced FAD—flavin adenine dinucleotide) are capable of forming the dye.

In clinical diagnostics, these dyes have been found to be invaluable for monitoring the formation of NAD(P)H from their parent compounds, NAD(P)+, in anaerobic reactions. (See, for example, U.S. Pat. No. 5,360,595, issued on Nov. 1, 1994 to D. Bell et al.) The redox reaction is rapid and is not sensitive to oxygen. The resulting dye color is very intense and has low solubility in water.

In principle, tetrazolium dye precursors can be used to measure ketone bodies and glucose in whole blood. However, the tetrazolium can be reduced non-enzymatically by hemoglobin (Fe(II)) to form a colored formazan, if the hemoglobin is not contained within the red cells of the blood. Thus, free hemoglobin causes serious interference with the measurements. In fact, due to hemolysis and the resultant abundance of free hemoglobin relative to the analyte of interest, in a typical ketone body measurement, the interfering signal from hemoglobin could exceed the intended signal. Glucose measurements, particularly in the normal concentration or above, are not affected as adversely. When the reaction is carried out in high hematocrit samples or at a higher temperature, where the hemoglobin oxidation reaction is faster, interference with glucose measurements is significant, as well. Since the hemolysis of red blood cells, which causes free hemoglobin to be present, cannot easily be avoided, red blood cells must be removed from samples prior to testing, if tetrazolium is to be used for the analysis.

Red blood cells can be removed from samples by filtering with membranes and filters, by trapping with chemical reagents, or by a combination of both methods. Filtration methods for separating red cells from whole blood are costly and require rather large sample volumes. An example of a blood ketone (beta-hydroxybutyrate) test that uses filtration to eliminate red cells from a whole blood sample is the KetoSite® test available from GDS Diagnostics, Elkhart, Ind. (See Tietz Textbook of Clinical Chemistry, $2^{nd}$ Ed., ed. by C. Burtis et al., W. B. Saunders Co., Philadelphia, Pa., 1994, p. 974.) The "Test Card" used in that test has two filter layers, which makes the card rather costly and necessitates a large (25 µL) blood sample. Further, the blood must not be hemolyzed.

A combination of filtration and chemical trapping is used in the Ames® Glucometer Encore™ blood glucose strip, available from Miles. That strip uses a layer of filter material and an agglutination aid (potato lectin) to eliminate interference from red cells. (See Chu et al., European Pat. Appl. 0 638 805 A2, publ. Feb. 15, 1995.)

Introducing an oxidizing agent into a system, to oxidize the hemoglobin to methemoglobin, is another way to reduce the hemoglobin interference. Although ferricyanides are known to transform hemoglobin to methemoglobin, they also destroy the desired product, NADH.

Palmer et al., EPO 0 330 517 B2, published on Aug. 30, 1989, disclose a method for measuring biochemical analytes that involves reacting the analyte with an oxidase enzyme capable of electron transferase activity with the analyte to yield reduced enzyme. The enzyme is colorimetrically assayed to determine the analyte concentration. The enzyme reaction is not oxygen-dependent.

Freitag et al., WO 94/01544, published on Jan. 20, 1994, disclose a stable reagent for analyte analysis. The reagent includes an enzyme, a phenazine derivative, a tetrazolium salt, and a divalent metal salt to stabilize the reagent.

Storhoff et al., WO 94/01578, published on Jan. 20, 1994, also disclose a stable reagent for analyte analysis. The reagent includes an enzyme, a mediator, a tetrazolium salt, and an oxidizing agent that stabilizes the reagent.

SUMMARY OF THE INVENTION

The present invention provides a reagent for measuring the concentration of an analyte in a hemoglobin-containing biological fluid. The reagent comprises:
  a) a flavin-dependent enzyme that has a flavin bound to it and that has specificity for the analyte,
  b) a tetrazolium dye precursor,
  c) an electron transfer agent, and
  d) a nitrite salt.
In an alternative embodiment of the invention, the reagent comprises;
  a) a flavin-dependent enzyme that has specificity for the analyte and does not have a flavin bound to it,
  b) flavin mononucleotide (FMN) or flavin adenine dinucleotide (FAD),
  c) a tetrazolium dye precursor,
  d) an electron transfer agent, and
  e) a nitrite salt.
The reagent is particularly suited for coating onto one or more substrates to form a dry reagent strip for measuring an analyte concentration in a hemoglobin-containing biological fluid. A particularly preferred strip comprises
  a) a support layer,
  b) on the support layer, a test pad having a coating that comprises
    i) a flavin-dependent enzyme that has a flavin bound to it and that has specificity for the analyte,
    ii) a tetrazolium dye precursor, and
    iii) an electron transfer agent, and
  c) on the test pad, a bibulous top layer that is coated with a nitrite salt.
Another strip of the invention comprises
  a) a support layer,
  b) on the support layer, a test pad having a coating that comprises
    i) a flavin-dependent enzyme that has specificity for the analyte and does not have a flavin bound to it,
    ii) FMN or FAD,
    iii) a tetrazolium dye precursor,
    iv) an electron transfer agent, and
  c) on the test pad, a bibulous top layer that is coated with a nitrite salt.

BRIEF DESCRIPTION OF THE DRAWINGS

FIG. 6 is a graph that shows the effect of nitrite as a hemoglobin suppressor on a single-layer glucose assay.

DETAILED DESCRIPTION OF THE INVENTION

The present invention provides a reagent for measuring analyte concentration in hemoglobin-containing biological fluids (such as whole blood), by producing a concentration of the reduced form of a cofactor, such as NADH, NAD(P)H, $PQQH_2$, $FMNH_2$, or $FADH_2$ that is a measure of the analyte concentration. Inclusion of nitrite in the reagent overcomes the interference of hemoglobin with the measurement of the reduced cofactor concentration. It is particularly useful for, but not limited to, measurement of ketone bodies and glucose.

Figure 1:
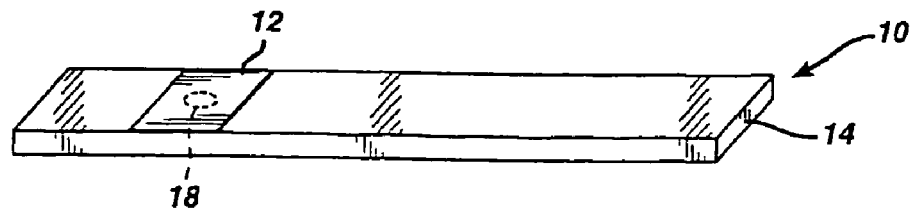
FIG. 1 is a perspective view of a test strip of this invention.

FIG. 1 depicts a typical test strip 10 of the invention, which consists of a test pad 12 affixed onto a support 14. The support may be a plastic—e.g., polystyrene, nylon, or polyester—or metallic sheet or any other suitable material known in the art. The test pad is coated with a reagent that reacts with the analyte to cause a color change. The test pad preferably comprises a bibulous material, such as filter paper or polymer membrane. However, since the reaction doesn't require oxygen, the test pad may be a non-bibulous material, such as plastic film. The reagent includes an enzyme that is specific to the analyte, a hydride transfer agent, a tetrazolium dye precursor, a suitable enzyme cofactor, and a hemoglobin suppressor. Optionally, a buffer and stabilizer are included for greater stability.

Figure 2:
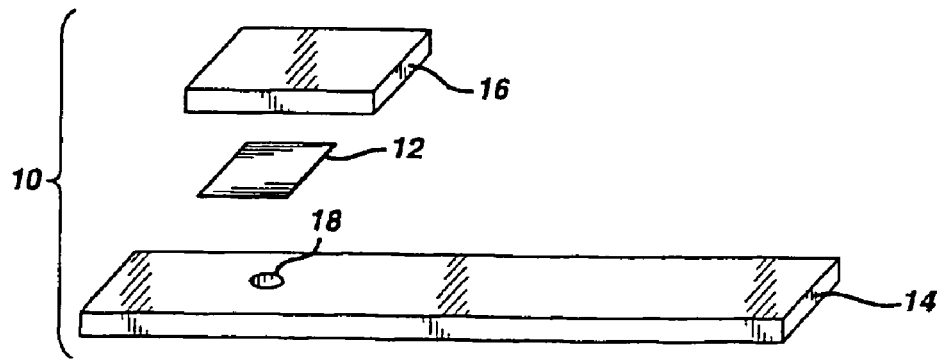
FIG. 2 is an exploded view of another test strip of this invention.

As shown in FIG. 2, the test strip can also be a multilayer construction, with top layer 16 overlaying test pad 12. In that construction, the reagent may be divided between the two layers. For example, the hemoglobin suppressor may be coated onto optional top layer 16 and the balance of the reagent coated onto test pad 12. Preferably, top layer 16 is bibulous and serves as a spreading layer and as an absorbent layer to absorb excess sample. Sample is applied to top layer 16, and it passes through to test pad 12. The analyte concentration is determined by measuring the color change through support layer 14 or, if layer 14 is not transparent where it adjoins the reaction area, through optional window or through-hole 18.

Figure 3:
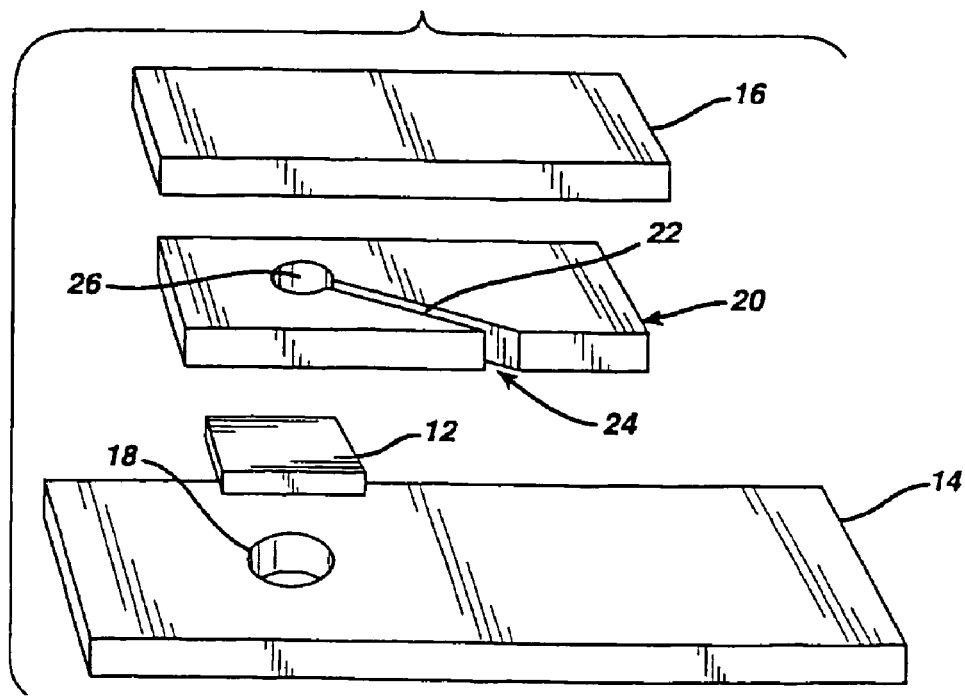
FIG. 3 is an exploded view of yet another test strip of this invention.

In the alternative embodiment shown in FIG. 3, spacer 20 separates top layer 16 and test pad 12. Spacer 20 is preferably a non-bibulous plastic film having an adhesive coating (not shown) on both faces. Channel 22 in spacer 20 provides a capillary path for sample to flow from opening 24 to measurement area 26. The flow depends on air venting between a surface of test pad 12 and an adjoining layer or, alternatively, through optional vent 18. The color change in measurement area 26 is monitored through optional vent/window 18. Reagent may all be on test pad 12 or, alternatively, may be divided among the test pad and one or both of non-bibulous layers 14 and 16. Thus, a first part of the reagent may be on the test pad and a second part of the reagent may be on one or both of the non-bibulous layers. When we refer to reagent as being a "coating" or "on" a layer, we intend to include the possibility that reagent will be absorbed into the layer, particularly if it is bibulous.

All flavin-dependent enzymes are suitable for assays with this invention. Suitable oxidase enzymes and their corresponding analytes include: alcohol oxidase for alcohol, glucose oxidase for glucose, galactose oxidase for galactose, cholesterol oxidase for cholesterol, L-lactate oxidase for L-lactate, urate oxidase for uric acid, bilirubin oxidase for bilirubin, and choline oxidase for choline. Suitable dehydrogenase enzymes and the corresponding analytes include: pyruvate dehydrogenase for pyruvate, D-lactate dehydrogenase for D-lactate, and succinate dehydrogenase for succinate.

When not bound to the enzyme, a cofactor must be added to activate the enzyme. Cofactors that may be added to a flavin-dependent enzyme include: flavin mononucleotide (FMN) and flavin adenine dinucleotide (FAD). In the presence of the enzyme, the analyte reduces the cofactor.

The next step in the dye-forming process is hydride abstraction from the reduced cofactor by an electron transfer agent. Suitable electron transfer agents include diaphorase, such as lipoic dehydrogenase, ferredoxin-NADP reductase, and lipoamide dehydrogenase. More preferred, when a flavin cofactor is used, are non-enzymatic electron transfer agents, such as phenazine methosulfate (PMS), phenazine ethosulfate (PES), 1-methoxyphenazine methosulfate, or Meldola Blue. Reaction kinetics and stability are the primary factors for selecting an electron transfer agent or "hydride abstractor". For example, PMS is the universal hydride abstractor, because it has relatively fast reaction kinetics with most of the tetrazolium compounds listed below. For that reason, it is preferred when the cofactor is PQQ. PMS is, however, more sensitive to light than enzyme-based hydride abstractors. Diaphorase is more stable and, for that reason, is preferred when the cofactor is NAD.

The captured hydride is transferred to a tetrazolium compound (dye precursor) to form a colored formazan. Tetrazolium compounds that are most suitable for this device are: 2-(2'benzothiazolyl)-5-styryl-3-(4'-phthalhydrazidyl) tetrazolium (BSPT), 2-benzothiazolyl-(2)-3,5-diphenyl tetrazolium (BTDP), 2,3-di(4-nitrophenyl) tetrazolium (DNP), 2,5-diphenyl-3-(4-styrylphenyl) tetrazolium (DPSP), distyryl nitroblue tetrazolium (DS-NBT), 3,3'-[3,3'-dimethoxy-(1,1'-biphenyl)-4,4'-diyl]-bis[2-(4-nitrophenyl)-5-phenyl(-2H tetrazolium (NBT), 3-(4,5-dimethyl-2-thiazolyl)-2,5-diphenyl-2H tetrazolium (MTT), 2-phenyl-3-(4-carboxyphenyl)-5-methyl tetrazolium (PCPM), tetrazolium blue (TB), thiocarbamyl nitroblue tetrazolium (TCNBT), tetranitroblue tetrazolium (TNBT), tetrazolium violet, (TV), 2-benzothiazothiazolyl-3-(4-carboxy-2-methoxyphenyl)-5-[4-(2-sulfoethylcarbamoyl)phenyl]-2H-tetrazolium (WST-4), and 2,2'-dibenzothiazolyl-5,5'-bis[4-di(2-sulfoethyl)carbamoylphenyl]-3,3'-(3,3'-dimethoxy-4,4'-biphenylene)ditetrazolium, disodium salt (WST-5). Preferably, water-soluble dye precursors, more preferably WST-5, are used so as to be compatible with biological samples. Further, when WST-5 is used, the resulting formazan compound exhibits strong spectral absorption at the purple-blue region, thus reducing the need for correcting the background signal from hemoglobin.

Finally, a hemoglobin suppressor is present in the reagent to curtail the undesirable dye-forming reaction between hemoglobin and the tetrazolium compound. The role of the hemoglobin suppressor is to oxidize the hemoglobin to methemoglobin, which does not react with the tetrazolium or formazan. Surprisingly, nitrite salts, such as sodium nitrite, potassium nitrite, and their derivatives, are very effective in suppressing the hemoglobin, while not destroying the reduced cofactor (such as NADH, $PQQH_2$, $FMNH_2$, or $FADH_2$). The nitrites are effective, as well, at elevated temperature and with high hematocrit samples. Sodium nitrite is preferred, because it has high aqueous solubility, is not toxic, and is relatively inexpensive.

Optionally, the reagent may also include a stabilizer, such as a divalent metal salt.

Although the reagent of this invention can be used in a wet chemical mode, such as in a cuvette, in preferred embodiments, the invention provides dry strips for assaying beta-hydroxybutyrate or glucose in whole blood. Strips may be either single-layer or two-layer. A two-layer strip consists of a membrane test pad, preferably of nylon, that is placed between a support and a top layer. The support is preferably of polyester sheet. The top layer can be a mesh or any bibulous material known in the art. A preferred material is a porous polyethylene treated with sodium methyl oleoyl taurate, available from the Porex Corp. of Fairburn, Ga. We refer to this material as "Porex". Preferably, the test pad has a positively-charged surface. More preferably, the test pad is polyamide. The test pad contains a reagent comprising glucose oxidase (including a flavin cofactor), PMS (or one of its analogs), and WST-5 (Table 1, below). The Porex top layer contains a nitrite reagent (Table 2).

In a single-layer strip, the Porex layer is omitted, and the entire reagent, including the nitrite (Table 3), is applied to the test pad. Note that in both the two-layer and single-layer strip, either a flavin-dependent enzyme that has a flavin bound to it or a flavin-dependent enzyme that does not have a flavin bound to it may be used. In the latter case, a flavin cofactor (e.g. FMN or FAD) is added.

Figure 4:
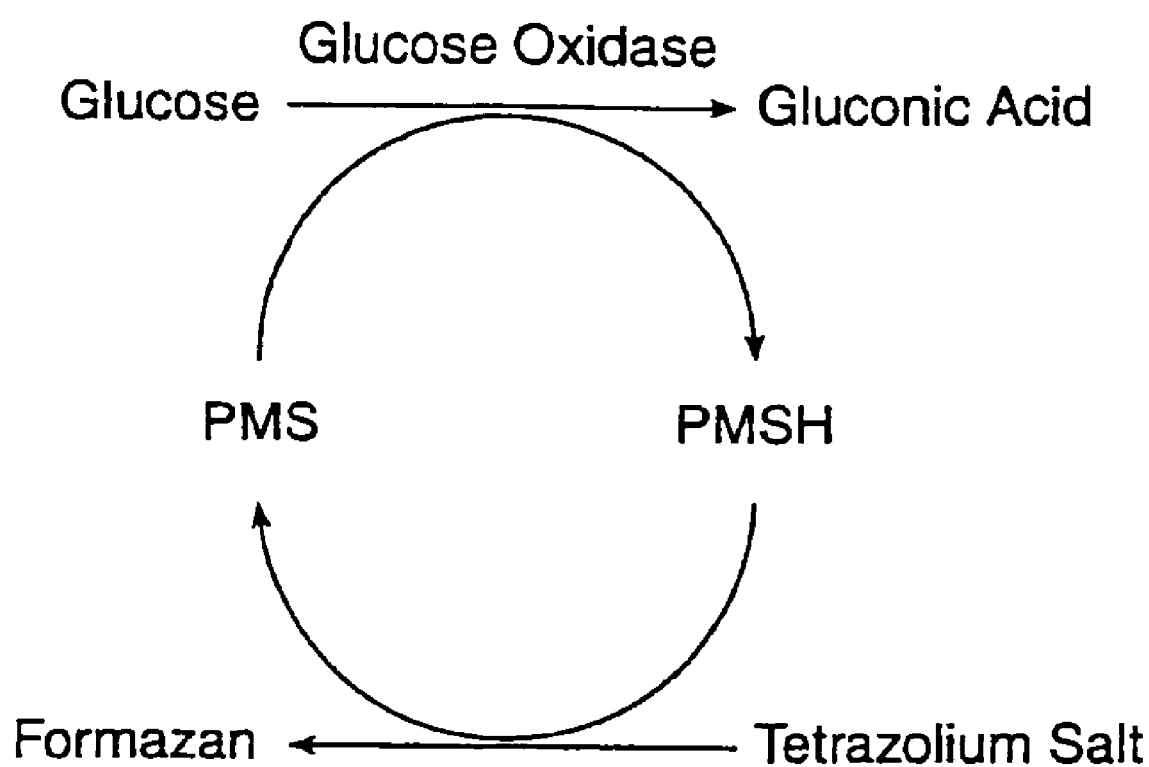
FIG. 4 is a pictorial depiction of the chemistry of a glucose assay of this invention.

In operation, a user applies a drop of whole blood to the upper surface of the Porex top layer. As the whole blood or lysed blood comes into contact with the Porex, the sodium nitrite is reconstituted and reacts with the available free hemoglobin, thus rendering the hemoglobin harmless to the assay. The resulting, substantially hemoglobin-free sample is transferred to the test pad below, via capillary or gravitational force. On the test pad, the sample initiates the cascade reaction to yield a colored dye, whose concentration is proportional to the analyte concentration in the sample and can be determined directly with a photometer. FIG. 4 depicts the reaction for glucose, using glucose oxidase and PMS.

Figure 5:
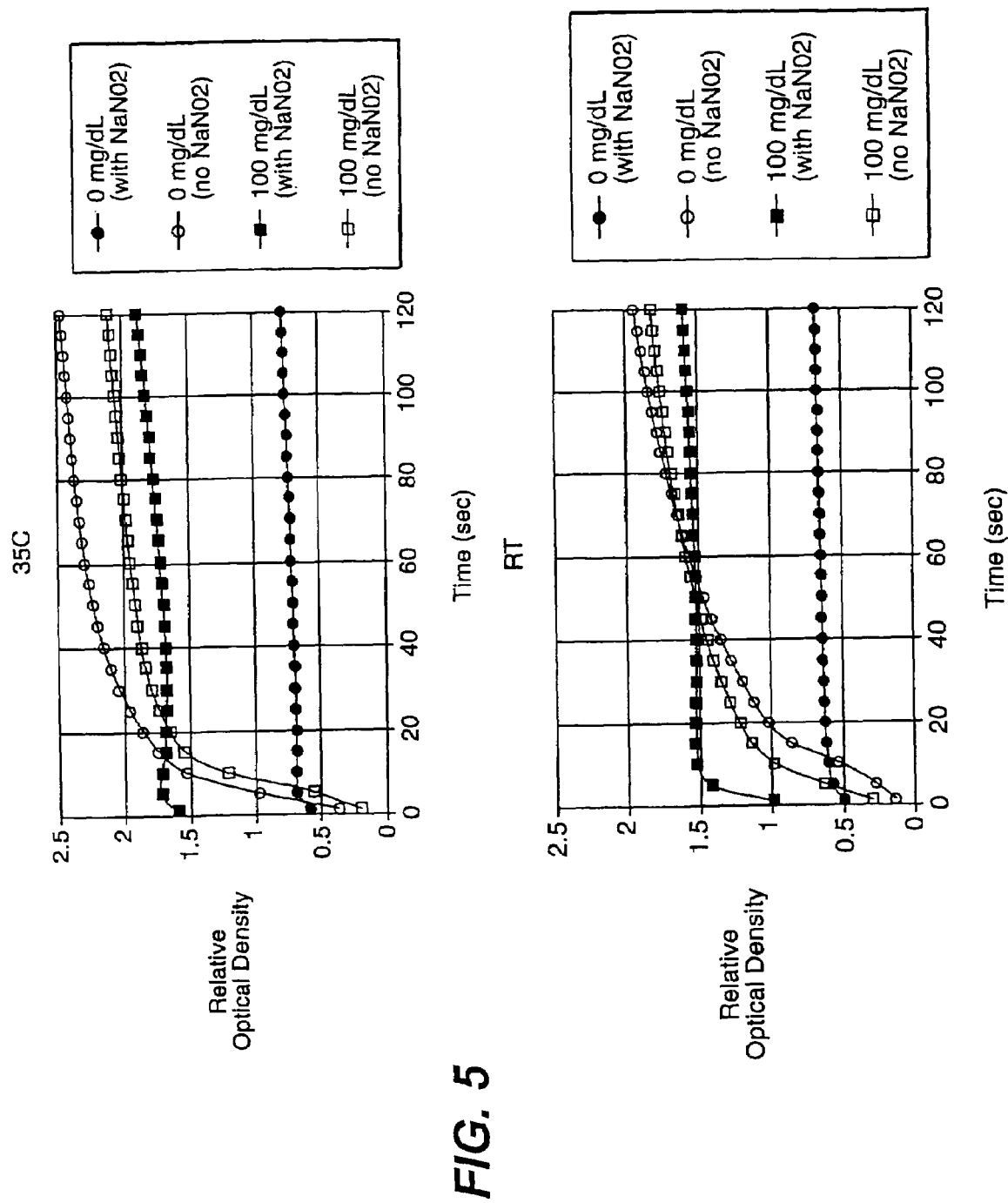
FIG. 5 is a graph that shows the effect of nitrite as a hemoglobin suppressor on a two-layer assay.

FIG. 5 depicts the change in optical density over time of blood samples, all having 60% hematocrit and containing 0 and 100 mg/dL of glucose, both with and without nitrite. The top graph displays results at 35° C. The bottom graph displays results at room temperature (RT). In each case, the nitrite concentration was 5 g/dL. In the absence of nitrite, hemoglobin reduces the tetrazolium to form a continuously increasing dye concentration, with a corresponding increase in optical density. Nitrite, by removing the hemoglobin (by oxidation), limits the color formation to that which results solely from the glucose in the sample. Preparation of the two-layer strip that was used to generate the data depicted in the graphs is described in Example 1, below.

FIG. 6 shows the effect of nitrite on the color-forming reaction in the glucose/glucose oxidase system for a single-layer strip. Blood samples, all having 60% hematocrit, contained 0 or 200 mg/dL of glucose and 0 or 20 mg/mL of nitrite. The samples were run at room temperature. The graph shows that the present system is effective at room temperature and hematocrit up to 60%. Preparation of the single-layer strip that was used is described in Example 2, below.

The following examples demonstrate preferred embodiments of the present invention. In Example 1, a two-layer strip was used, the analyte is glucose, and the enzyme is glucose oxidase. In Example 2, a single-layer strip was used. As before, the analyte is glucose and the enzyme is glucose oxidase. The compositions can readily be modified for application to other analyte-enzyme combinations listed earlier. (See, for example, *Tietz Textbook of Clinical Chemistry*, $2^{nd}$ Ed., ed. by C. Burtis et al., W. B. Saunders Co., Philadelphia, Pa., 1994, pp 976–978 and 1174–1175.) The examples are not intended to be in any way limiting.

EXAMPLE 1

A 0.8 μm nylon membrane obtained from Pall Corporation (East Hills, N.Y.) was dipped into the reagent of Table 1, until saturated. The excess reagent was scraped off gently with a glass rod. The resulting membrane was hung to dry in a 56° C. oven for 10 minutes. Porex (0.6 mm thick) was soaked in the nitrite solution of Table 2 and then hung to dry in a 100° C. oven for ten hours. Finally, the membrane was laminated between a polyester stock (0.4 mm Melenex® polyester from ICI America, Wilmington, Del.) and the nitrite-impregnated Porex.

EXAMPLE 2

The procedure of Example 1 was repeated, except that the first dip was the reagent of Table 3, and there was no second dip, since the Porex was not needed.

TABLE 1

Reagent for a Glucose Test Pad

| Components | Quantity |
|---|---|
| Water | 100 ml |
| (2-[-Morpholino]ethanesulfonic acid) sodium salt MES (MW 217.2, Sigma, St. Louis, MO, USA) Adjust pH to 5–7 by adding 6 M HCl) | 2.2 gm |
| Tetonic 1307 (BASF Corporation, Moun Olive, New Jersey, USA) | 1–3 gm |
| PSSA, Polystyrenesulfonic acid, sodium salt (MW 70,000, Polysciences, Inc., Warrington, PA, USA) | 2–4 gm |
| Crotein (Croda Inc., Parsippany, NJ, USA) | 2–4 gm |
| Mannitol (MW 182, Sigma, St. Louis, MO, USA) | 1–10 gm |
| Phenazine Methosulfate (PMS, MW 306.34, Sigma, St. Louis, MO, USA | 30–300 mg |
| WST-5 (MW 1331.37, Dojindo) | 0.8–4 gm |
| Glucose Oxidase (GO, TOYOBO) | 100–1000 KU |

TABLE 2

Nitrite Reagent

| Components | Quantity |
|---|---|
| 10 mM Phosphate Buffer Saline, pH7.4, (P-3813, Sigma, St. Louis, MO, USA) | 70 ml |
| Ethanol | 30 ml |
| Sodium Nitrite (MW69, Aldrich Chemicals, Milwaukee, WI, USA) | 5 gm |
| Polyvinylpyrrodine (MW 40,000, Sigma, St. Louis, MO, USA) | 200 mg |

TABLE 3

Reagent for a Glucose Test Pad

| Components | Quantity |
|---|---|
| Water | 100 ml |
| (2-[-Morpholino]ethanesulfonic acid) sodium salt MES (MW 217.2, Sigma, St. Louis, MO, USA) | 2.2 gm |
| Gantrez* 6% | 20 mL |
| Adjust pH to 5.5–7 by adding 50% NaOH | |
| Triton X-305 (BASF Corporation, Moun Olive, New Jersey, USA) | 0.5–2 gm |
| Mannitol (MW 182, Sigma, St. Louis, MO, USA) | 1–10 gm |
| Sodium Nitrite (MW69, Aldirch Chemicals, Milwaukee, WI, USA | 1–5 gm |
| WST-5 (MW 1331.37, Dojindo) | 0.8–4 gm |
| Magnesium Chloride (MW 203, Sigma, St. Louis, MO, USA) | 3–5 gm |
| Phenazine Ethosulfate (PES, MW 334.4, Sigma, St. Louis, MO, USA) | 100–1000 mg |
| Glucose Oxidase (GO, TOYOBO) | 100–1000 KU |

*Gantrez AN-139 (Poly Methylvinylether-alt-Maleic Anhydride, MW 1,080,000, Cat# 41632-0, Aldrich Chemicals, Milwaukee, WI, USA) Make 6% Gantrez in water, heat to 95 C. for less than 45 min. to get Gantrez 6% which is ready to use.

We claim:

1. A reagent for measuring a concentration of an analyte in a hemoglobin-containing biological fluid, comprising
   (a) a flavin-dependent enzyme that has a specificity for the analyte and does not have a flavin bound to it,
   (b) a flavin mononucleotide (FMN) or flavin adenine dinucleotide (FAD),
   (c) a tetrazolium dye precursor,
   (d) an electron transfer agent, and
   (e) a nitrite salt.

2. The reagent of claim 1 in which the dye precursor is water-soluble.

3. The reagent of claim 1 in which the electron transfer agent comprises phenazine methosulfate (PMS) or an analog thereof.

4. The reagent of claim 1 further comprising a divalent metal stabilizer.

* * * * *